United States Patent [19]

Hammond et al.

[11] Patent Number: 5,043,263
[45] Date of Patent: Aug. 27, 1991

[54] MONOCLONAL ANTIBODIES AGAINST POTYVIRUS-ASSOCIATED ANTIGENS, HYBRID CELL LINES PRODUCING THESE ANTIBODIES, AND USE THEREFORE

[76] Inventors: John Hammond, 9217 Twin Hill La., Laurel, Md. 20708; Ramon L. Jordan, Jr., 8715 Clemente Ct., Jessup, Md. 20794

[21] Appl. No.: 527,638

[22] Filed: May 24, 1990

Related U.S. Application Data

[63] Continuation of Ser. No. 82,591, Aug. 7, 1987, abandoned.

[51] Int. Cl.[5] .................... C12Q 1/70; G01N 33/53; G01N 33/536; G01N 33/569
[52] U.S. Cl. ..................................... 435/5; 435/7.9; 435/70.21; 435/172.2; 435/235.1; 435/240.27; 435/948; 436/536; 436/542; 436/548; 436/172; 530/387; 530/809
[58] Field of Search ............... 435/5, 7, 70.2, 70.21, 435/172.2, 235, 240.26, 240.27, 948; 530/387, 809; 436/548, 536, 542, 172, 804

[56] References Cited

PUBLICATIONS

Gugerli et al., J. Gen. Virol., vol. 64:2471-2477 (1983).
Hill et al., J. Gen. Virol., vol. 65:525-532 (1984).
Dougherty et al., Virology, vol. 144:66-72 (1985).
Shephard et al., Virology, vol. 58:464-475 (1974).

Primary Examiner—Esther L. Kepplinger
Assistant Examiner—Janelle Graeter
Attorney, Agent, or Firm—Banner, Birch, McKie & Beckett

[57] ABSTRACT

The present invention is directed to monoclonal antibodies, and hybridomas which produce them, which are reactive with a highly conserved epitope present on potyviruses and insignificantly reactive with other plant viruses, as well methods of using these monoclonal antibodies to detect potyviruses.

8 Claims, No Drawings

MONOCLONAL ANTIBODIES AGAINST POTYVIRUS-ASSOCIATED ANTIGENS, HYBRID CELL LINES PRODUCING THESE ANTIBODIES, AND USE THEREFORE

This application is a continuation of application Ser. No. 082,591, now abandoned, filed Aug. 7, 1987.

BACKGROUND OF THE INVENTION

1. Field of the Invention

This invention is directed to monoclonal antibodies against antigens associated with potyviruses, hybrid cell lines producing these antibodies, and methods of using these monoclonal antibodies.

2. Description of the Background Art

The potyviruses are a group of aphid transmitted plant viruses with flexuous filamentous particles that are 680–900 nm long and about 11 mm in diameter. The virions typically are composed of up to about 2,000 subunits of a single capsid protein species which has a molecular weight of about 32–36 Kd. The capsid proteins are arranged in a helix which encloses the genome. The viruses induce the formation of characteristic cytoplasmic inclusions which are serologically unreleated to their respective viral capsid protein.

Members of the potyvirus group comprise the largest and economically most important group of plant viruses and affect a wide range of crop plants. Thus, the detection of these viruses would be of considerable interest.

Among those techniques of interest for use in detecting potyviruses are those which involve the use of antibodies. Serological relationships among potyviruses are, however, highly complex. Most of the definitive potyviruses have been shown to be serologically related to some degree to at least one other potyvirus, but present techniques have failed to detect any relationship between many potyviruses. Polyclonal antisera show cross-reactivity to various degrees with only a few closely related virus strains of the same virus used to immunize and fail to cross-react with more distantly related viruses. Polyclonal antisera produced to denatured potyviruses, however, show a higher degree of cross-reactivity with different potyviruses. (Shepard, et al., *Virology*, 58:464, 1974). Monoclonal antibodies produced to specific potyvirus members have proven to be specific for the immunizing virus or show only limited cross-reactivity with less related potyviruses (Dougherty, et al., *Virology*, 144:66, 1985; Gugerli, et al., *Journal of General Virology*, 64:2471, 1983; Hill, et al., *Journal of General Virology*, 65:525, 1984).

As a result of the lack of broadly reactive antibodies specific to potyviruses, at present it would be extremely difficult to design an effective immunodiagnostic test for their detection. This is because immunodiagnostic tests using existing antibodies would require either multiple assays or the use of pooled antibody reagents in order to attempt detection of most potyviruses encountered in ecological samples. Unfortunately, it is unlikely that either of these approaches are feasible since using multiple assays is cumbersome and inefficient and the use of pooled antibody reagents is inherently likely to result in a loss of sensitivity. As a consequence, a considerable need remains for a antibody which is broadly reactive with potyviruses, but not other plant viruses, that can be used immunodiagnostically.

SUMMARY OF THE INVENTION

It is an object of the present invention to provide a monoclonal antibody that is capable of reacting with potyviruses, but shows insignificant reactivity with other plant viruses, for purposes of effective diagnosis of diseases caused by these plant viruses.

It is another object of the present invention to provide methods for the diagnosis of potyvirus disease using monoclonal antibodies which react with potyviruses, but not other plant viruses.

The present invention thus relates to monoclonal antibodies reactive with a highly conserved epitope present on 61 strains of potyviruses, but which are insignificantly reactive with other plant viruses. The invention further includes hybrid cell lines which produce these antibodies, as well as methods of using and processes of preparing these monoclonal antibodies.

DETAILED DESCRIPTION

The present invention relates to monoclonal antibodies for antigen indicative of potyviruses. These monoclonal antibodies are highly useful for immunological detection of antigens associated with potyvirus infection.

In particular, the present invention provides a monoclonal antibody specifically reactive with an epitope found on at least 26 distinct potyvirus types of the potyvirus group and insignificantly reactive with other plant viruses, where the epitope is specifically bound by the monoclonal antibody produced by cell line ATCC HB 9452, as well as hybrid cell lines producing such antibodies.

The general method used for production of hybridomas secreting monoclonal antibodies is well known to those of ordinary skill in the art. Illustrative of the techniques utilized in the present invention are those described in *Proceedings of the National Academy of Science, U.S.A.*, 75:3405, (1978).

In brief, female BALB/c mice were immunized over a six month period with pooled potyvirus immunogens. After the final immunization, the animals were sacrificed and spleen cells fused with a mouse non-secretor myeloma cell line. Hybridomas were screened for antibody production and positive clones were tested for monoclonal antibody binding to various potyviruses.

The isolation of other hybridomas secreting monoclonal antibodies with the specificity of the monoclonal antibodies of the invention can be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunized the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

Alternatively, it is possible to evaluate, without undue experimentation, a monoclonal antibody to determine whether it has the same specificity as the monoclonal antibody of the invention by determining whether the monoclonal antibody being tested prevents the monoclonal antibody of the invention from binding to a particular antigen, or virus, with which the monoclonal antibody of the invention is normally reactive. If the monoclonal antibody being tested competes with the monoclonal antibody of the invention, as shown by a decrease in binding by the monoclonal antibody of the invention, then it is considered that the two monoclonal antibodies bind to the same epitope. Also, a monoclonal antibody can be tested for the same reactivity pattern for potyviruses as PTY-1.

Under certain circumstances, monoclonal antibodies of one isotype might be more preferable than those of another in terms of their diagnostic efficacy. Particular isotypes of a monoclonal antibody can be prepared either directly, by selecting from the initial fusion, or prepared secondarily, from a parental hybridoma secreting monoclonal antibody of different isotype by using the sib selection technique to isolate class-switch variants (Steplewski, et al., *Proceedings of National Academy of Science, U.S.A.*, 82:8653, 1985; Spira, et al., *Journal of Immunological Methods*, 74:307, 1984). Thus, the monoclonal antibodies of the invention would include class-switch variants having the specificity of monoclonal antibody PTY-1 which is produced by ATCC HB 9452.

The term "antibody" as used in this invention is meant to include intact molecules as well as fragments specific binding thereof, such as, for example, Fab and F(ab')$_2$, which are capable of binding the epitopic determinant.

The monoclonal antibodies of the invention are particularly suited for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Regardless of the type of immunoassay which is used, the concentration of antibody utilized can be readily determined by one of skill in the art.

The monoclonal antibodies of the invention can be bound to many different carriers and used to detect the presence of potyvirus-associated antigen. Examples of well-known carriers include glass, polystyrene, polyvinyl chloride, polypropylene, polyethylene, polycarbonate, dextran, nylon, amylases, natural and modified celluloses, polyacrylamides, agaroses and magnetite. The nature of the carrier can be either soluble or insoluble for purposes of the invention. Those skilled in the art will known of other suitable carriers for binding monoclonal antibody, or will be able to ascertain such, using routine experimentation.

There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds. Those of ordinary skill in the art will known of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purpose of the invention, the potyvirus-associated antigen which is detected by the monoclonal antibodies of the invention may be present in plant fluids and tissues. Any sample containing a detectable amount of potyvirus-associated antigen can be used, including purified native and denatured virus, capsid protein and protein fragments or peptides that contain the epitope recognized by the monoclonal antibody of the invention, as well as proteins or peptides containing the epitope produced by genetically engineered organisms expressing a potyviral capsid protein gene.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chain and usually have specific three dimensional structural characteristics, as well as specific charge characteristics.

The term "diagnostically effective" means that the amount of monoclonal antibody is in sufficient quantity to enable detection of potyvirus antigen having the epitope for which the monoclonal antibodies of the invention are specific.

The term "preferentially reactive" means that the monoclonal antibodies of the invention can distinguish between a potyvirus and another plant virus or normal plant tissue. The term "insignificantly reactive" means that the degree of reactivity seen between the monoclonal antibody of the invention and other plant viruses does not hinder the diagnostic or usefulness of the monoclonal antibody. For example, when used diagnostically the monoclonal antibodies of the invention bind so much more significantly to potyvirus as compared to other plant viruses that the potyvirus infected tissues are clearly distinguishable from any background due to binding of the antibodies to other plant viruses or uninfected normal plant tissue.

Monoclonal antibody PTY 1 can be utilized in the present invention. PTY 1 is obtained from, or has the identifying characteristics of, an antibody obtained from the cell line 31F2 having ATCC accession number HB 9452. This cell line was placed on deposit for 30 years at the American Type Culture Collection (ATCC) in Rockville, Md. prior to Aug. 7, 1987.

The above disclosure generally describes the present invention. A more complete understanding can be obtained by reference to the following specific examples which are provided herein for purposes of illustration only, and are not intended to limit the scope of the invention.

EXAMPLE 1

PREPARATION OF HYBRIDOMA CELL LINES PRODUCING MONOCLONAL ANTIBODIES TO POTYVIRUSES

A. Viral and Cytoplasmic Inclusion Purification

All viruses were purified from freshly harvested pea, tobacco, Iris or Belamcanda. The purification procedure incorporates the Triton X-100 clarification introduced by van Oosten (*Netherlands Journal of Plant Pathology*, 78:33, 1972,) while the cylindrical inclusion preparation was adapted from that of Dougherty and Hiebert (*Virology*, 104:174, 1980). Purifications were made when indicated by symptom expression and convenience; usually 20–40 days after inoculation by standard methods. Tissue was homogenized in 3–5 volumes of chilled 0.5M $K_2H$ $PO_4/KH_2PO_4$ PH 8.4 containing 0.5% (w/v) $Na_2SO_3$ and filtered through cheesecloth, and centrifuged at 3300 g for 10 min. (Sorvall GSA rotor). The supernatant was collected, Triton X-100 added to 2% (v/v), prior to the addition of NaCl to 0.1M and polyethylene glycol (PEG; molecular weight 8000) to 4% (w/v), followed by stirring for 1 h. The PEG precipitated material was collected by centrifugation at 8000 g for 10 min. (Sorvall GSA rotor). The precipitate was resuspended in 0.1M boric acid, 0.1M KCl adjusted to pH 8.0 with NaOH (BK buffer) and clarified by centrifugation at 8000 g for 10 min. The pellet was retained for purification of the cytoplasmac inclusion protein (see below), while 25 ml of supernatant per 30 ml Oak Ridge tube was carefully underlaid with 5 ml of 30% (w/v) sucrose in BK buffer followed by centrifugation at 85600 g for 2.5 h in a Beckman Type 30 rotor. The pellets were resuspended in buffer and homogenized with a Potter-Elvehejm tissue grinder either immediately or after soaking overnight. The virus suspension was then adjusted to 23 ml with BK buffer, and 10 g of CsCl gently dissolved in it (forming a median density of approx. 1.32 g. $cm^{-3}$). Alternatively, 7.5 g of $Cs_2SO_4$ was added, as some potyvirus isolates are sensitive to CsCl. A density gradient was formed by centrifugation at 139000 g for 16-20 h, at either 10° or 20° (Beckman Type 65 rotor). Virus peak fractions were collected by hand, and dialyzed against three changes of 1 liter of 0.5× BK buffer. All virus yields were calculated on the basis $E°^{0.1\%}1$ cm 260 nm=2.5.

The cytoplasmic inclusion protein (CIP) pellets from above were resuspended in 38 ml each of 20 mM $K_2H/KH_2PO_4$ pH 8.4 containing 0.1% 2-mercaptoethanol (PME buffer) and homogenized in a small blender. Triton X-100 was then added to a final concentration of 5% (v/v) prior to collection of the inclusions by centrifugation at 27000 g (Sorval SS-34 rotor) for 20 min. The pellets were resuspended in PME, vortexed, and stirred until dissolved. The inclusions were collected by centrifugation as before, resuspended in PME and stirred until dissolved. Aliquots of 7.5 ml were layered over 4.5 ml of 80% (w/v) sucrose in PME in 12 ml tubes, which were centrifuged at 154000 g for 1 hour (Beckman SW 41 rotor). The inclusions were collected from the interface of the sample and 80% sucrose layers with a Pasteur pipet, diluted with 20 mM Tris-HCl pH 8.2, and precipitated by centrifugation as before. The final pellets were resuspended in a small volume of 20 mM Tris-HCl pH 8.2.

All steps of virus and inclusion preparations were carried out at 4°, except as noted.

B. Immunization and Production of Hybridomas

Female Balb/c mice were immunized with a mixture of up to 14 serologically related and unrelated potyviruses as outlined in TABLE 1. Eight days before the first immunization, the mice were primed with pristane (0.5 ml).

Five days after the final immunization (day 203) the mice were sacrificed and their spleens aseptically separated. Using standard methods, splenic lymphocytes were fused with myeloma cell line P3-NS1-Ag-4-1 in the presence of 45% polyethylene glycol and the fusion product cultured in RPMI-1640 with 15% fetal bovine serum. Individual hybridoma clones were isolated using limiting dilution.

TABLE 1

| | | | | IMMUNIZATION PROTOCOL | | | |
|---|---|---|---|---|---|---|---|
| | | | | IMMUNOGEN DOSE[c] | | | |
| | | | | INTACT VIRUS | | C.I.P. | |
| INJECTION[a] | DAY[b] | VIRUSES | ADJUVANT | NATIVE | DENAT. | NATIVE | DENAT. |
| 1 | 0 | BYMV-GDD | FCA | 50 | — | 50 | — |
| 2[d] | 22 | BYMV-GDD | IFA | — | 50 | — | 50 |
| 3[e] | 120 | BYMV-GDD | IFA | — | 18 | — | 2 |
| | | IMMV | | — | 28 | — | 3 |
| | | ISMV | | — | 9 | — | 1 |
| | | Wa Tulip | | 4 | — | 16 | — |
| | | G82-18 | | 5 | — | 5 | — |
| | | BYMV-Iris | | 5 | — | 5 | — |
| | | PVY | | 10 | — | 10 | — |
| | | BCMV | | 2 | — | 8 | — |
| | | AV-1 | | 12 | — | 9 | — |
| 4[f] | 125 | BYMV-GDD | IFA | — | 18 | — | 2 |
| | | IMMV | | — | 28 | — | 3 |
| | | ISMV | | — | 9 | — | 1 |
| | | Wa Tulip | | — | 2 | — | 8 |
| | | G82-18 | | — | 3 | — | 3 |
| | | BYMV-Iris | | — | 3 | — | 3 |
| | | PVY | | — | 5 | — | 5 |

TABLE 1-continued

IMMUNIZATION PROTOCOL

| | | | | IMMUNOGEN DOSE[c] | | | |
|---|---|---|---|---|---|---|---|
| | | | | INTACT VIRUS | | C.I.P. | |
| INJECTION[a] | DAY[b] | VIRUSES | ADJUVANT | NATIVE | DENAT. | NATIVE | DENAT. |
| | | BCMV | | — | 1 | — | 4 |
| | | AV-1 | | — | 6 | — | 5 |
| | | PSbMV | | — | 12 | — | 50 |
| | | TEV | | — | 50 | — | 50 |
| 5[g] | 147 | BYMV-GDD | NONE[h] | 13 | 26 | 8 | 17 |
| | | IMMV | | 8 | 17 | 1 | 2 |
| | | ISMV | | 3 | 5 | 1 | 1 |
| | | Wa Tulip | | 1 | 3 | 3 | 5 |
| | | G82-18 | | 1 | 2 | 1 | 2 |
| | | BYMV-Iris | | 1 | 2 | 1 | 2 |
| | | PVY | | 2 | 3 | 2 | 3 |
| | | BCMV | | 1 | 1 | 1 | 3 |
| | | AV-1 | | 2 | 4 | 2 | 3 |
| | | PSbMV | | 4 | 8 | 17 | 33 |
| | | TEV | | 7 | 33 | 17 | 33 |
| 6[a] | 198 | BYMV-GDD | NONE[h] | — | 73 | — | 37 |
| | | GOLDFIELD | | — | 10 | — | — |
| | | 49er | | — | 10 | — | — |
| | | G82-18 | | — | 7 | — | 3 |
| | | Ideal A | | — | 4 | — | — |
| | | Wa Tulip | | — | 12 | — | 8 |
| | | IMMV | | — | 38 | — | 5 |
| | | ISMV | | — | 9 | — | 2 |
| | | BYMV-Iris | | — | 3 | — | 3 |
| | | PVY | | — | 5 | — | 5 |
| | | BCMV | | — | 1 | — | 4 |
| | | AV-1 | | — | 13 | — | 5 |
| | | PSbMV | | — | 12 | — | 50 |
| | | TEV | | — | 50 | — | 50 |

[a]300 ul, intraperitoneally
[b]days after first immunization
[c]ug protein
[d]denatured immunogen prepared by treating pH 9.5, 56° C., 15 min.
[e]denatured immunogen prepared by treating 2% SDS, 5% 2-ME, 95° C., 10 min., ppt. with 5 vol. acetone, −20° C., overnight; centrifuge (8,000 G, 10 min.), resuspend pH 8.2
[f]denatured immunogen prepared by treating 56° C., 15 min.
[g]denatured immunogen prepared by treating ppt. with acetone as in (e), resuspend pellet at pH 7.5; raise to pH 11.5, 10 min.; lower to pH 7.5
[h]in 20 mM tris, 150 mM NaCl, pH 7.5

EXAMPLE 2

CHARACTERIZATION OF MONOCLONAL ANTIBODIES REACTIVE WITH VARIOUS POTYVIRUSES

A. Initial Screening

After the initial cell culture, 764 of 1728 microtiter wells had growth. The culture supernatants from these wells were initially screened using standard enzyme-linked immunosorbant assay (ELISA) conditions on polyvinyl chloride microtiter plates coated with four different antigen preparations.

Antigen preparation A was prepared from potyviruses TuMV, SMV, PSbMV, PVY, TEV, BYMV-GDD, BYMV-Goldfield, BYMV-49er, BYMV-G82-18, BYMV-Ideal and BYMV-Wa Tulip. A stock antigen solution containing equal quantities of antigen derived from these viruses was prepared. This stock solution contained equal concentrations of native virus and denatured virus. The denatured viral material was treated with 0.2% SDS, at 56° C. for 15 minutes. 4.8 ug of antigen mixture in 100 ul (20 mM tris, 150 mM NaCl, pH 7.5 (TBS)) was added to each well.

Antigen preparation B was prepared from potyviruses BYMV-GDD, BYMV-G82-18, BYMV-Iris, BYMV-Wa Tulip, TEV, PVY, PSbMV, SMV, BCMV, AV-1, ISMV and IMMV. A stock solution was prepared which contained equal concentrations of denatured viruses and denatured CIP. Denaturation was carried out as for preparation A. 2.0 ug of antigen mixture in 100 ul TBS was added to each microtiter well.

Antigen preparation C was prepared from potyviruses IMMV, ISMV, and AV-1. This preparation was composed of equal concentrations of native and denatured virus and native and denatured CIP. Denatured material was prepared as described in antigen preparation A. 2.4 ug in 100 ul TBS of the antigen mixture was added to each well of microtiter the plate.

Antigen preparation D was prepared from healthy pea, tobacco plants, Iris and Belamcanda. This protein material was prepared in the same manner as the viral immunogen purification described in Example 1, A, above. 5.0 ug of antigen solution in 100 ul TBS was added to each well of the microtiter plate.

In the initial screens, 73 hybridomas produced antibodies reactive with at least one of viral antigen preparations A, B, or C, while showing no reactivity with control preparation D.

The monoclonal antibodies from these 73 hybridomas were then tested against antigen preparation A and E. Antigen preparation E was composed of equal concentrations of denatured CIP from potyviruses BYMV-GDD, BYMV-G82-18, BYMV-Iris, BYMV-Wa Tulip, TEV, PVY, SMV, BCMV, AV-1, ISMV and IMMV. Denaturation was carried out as for preparation A. 4.0 ug in 100 ul TBS of the antigen mixture was added to each well of the microtiter plate.

The 24 hybridomas that produced monoclonal antibodies reactive only to preparation E (that is, only to CIP) subsequently stopped producing antibody. In addition, 6 of the remaining 49 hybridomas that produced monoclonal antibody reactive only to preparation A (that is, a mixture of native and denatured virus) also subsequently stopped producing antibody.

B. SECONDARY SCREEN

Following the initial screens the monoclonal antibodies from the remaining 43 hybridomas were screened against individual plant virus preparations containing equal amounts of native and denatured virus using the following procedure.

Polystyrene microtiter plates were coated with purified virus (0.2 ug/well in 100 ul, 0.05 m carbonate buffer, pH 9.6) and incubated for 2-5 hours at room temperatures. The plates were emptied and washed twice (5 min. each) with tris-buffered saline containing 0.05% Tween-20 (TBS/T). After washing, the plates were filled with TBS containing 0.5% BSA and 1% powdered milk (TBS/B) for at least 1 hour at room temperature, then washed again with TBS/T. Individual monoclonal antibodies were diluted (1:10 for culture supernatants and 1:5,000-1:25,000 for ascites) in TBS with 0.1% powdered milk and 0.05% BSA (TBS/0.1 B) and 100 ul added to the respective microtiter wells. The plates were incubated overnight at 6° C. then washed four times with TBS/T (5 min. each wash). Alkaline-phosphatase conjugated goat anti-mouse (Kirkegaard & Perry Laboratories, Gaithersburg, Md.) diluted 1:2000 in TBS/0.1 B was added (100 ul) to each well and incubated at room temperature for 2-3 hours. Next, the plates were washed five times (5 min. each) and p-nitrophenylphosphate (PNPP in diethanolamine buffer at 1.0 mg/ml) added to each well (150 ul). Plates were incubated at room temperature for 1 hour and read at 405 mm.

Under these conditions, the monoclonal antibody PTY 1, from hybridoma 31F2 was found to react with all potyviruses tested. The remaining 42 hybridomas produced monoclonal antibodies that had a range of differential reactivity with the potyviruses tested; from reactivity with only 1 potyvirus strain, to reactivity to 26 of 32 potyvirus strains tested. Further testing of PTY 1 has shown that it is capable of detecting all 61 potyvirus strains, representing 26 distinct potyvirus types, tested to data (TABLE 2). PTY 1 can detect potyviruses when the virus is present in purified form or when present in infected tissue such as, for example, crude plant sap extract or as isolated capsid protein from virus or from genetically engineered organisms expressing potyviral capsid protein genes.

In addition, PTY 1 does not react with such non-potyviruses as, for example, tobacco mosaic virus (tobamovirus), tomato ring spot and tobacco ring spot viruses (nepoviruses), cucumber mosaic virus (cucumovirus), chrysanthemum virus B and lily symptomless virus (carla viruses), cymbidium mosaic virus (potexvirus), carnation necrotic fleck virus (closterovirus), carnation mottle virus (carmovirus), apple mosaic and prunus necrotic ringspot viruses (ilarviruses), wheat spindle streak mosaic virus (potyviral-like virus transmitted by fungi) and sweet potato disease virus (non-potyvirus whitefly-component). Thus, the epitope recognized by PTY 1 appears to be highly conserved among members of the potyvirus family and not present in other plant viruses or in normal plant tissue.

Further characterization of PTY 1 has shown that it recognizes an epitope on the potyvirus structural capsid protein which is more accessible in denatured virus or purified or denatured capsid protein than with intact virions. In addition, the binding of PTY 1 antibody to denatured virus can be inhibited by molar concentrations of purified native and denatured capsid protein, but not by intact virions. These findings suggest that the epitope faces internally in the intact virion.

The invention now being fully described, it will be apparent to one of ordinary skill in the art that many changes and modifications can be made without departing from the spirit or scope of the invention.

TABLE 2

POTYVIRUSES REACTIVE WITH MONOCLONAL ANTIBODY PTY 1

| VIRUS | ABBREVIATION |
|---|---|
| Asparagus virus 1 (2 strains tested) | AV-1 |
| Bean common mosaic virus (4 strains tested) | BCMV |
| Bean yellow mosaic virus (10 strains tested) | BYMV |
| Blackeye cowpea mosaic virus (3 strains tested) | BlCMV |
| Celery mosaic virus | CelMoV |
| Clover yellow vein virus | CYVV |
| Cowpea aphid-borne mosaic virus (3 strains tested) | CAbMV |
| Iris mild mosaic virus | IMMV |
| Iris severe mosaic virus (2 strains tested) | ISMV |
| Lettuce mosaic virus | LMV |
| Maize dwarf mosaic virus (2 strains tested) | MDMV |
| Papaya ringspot virus | PRV |
| Pea mosaic virus (2 strains tested) | PMV |
| Pea seed-borne mosaic-virus (2 strains tested) | PSbMV |
| Pepper mottle virus | PeMV |
| Plum pox virus | PPV |
| Potato virus Y (type member) | PVY |
| Soybean mosaic virus | SMV |
| Statice virus Y (2 strains tested) | StVY |
| Sugarcane mosaic virus (4 strains tested) | SCMV |
| Sweet potato feathery mottle virus (4 strains tested) | SPFMV |
| Tobacco etch virus (3 strains tested) | TEV |
| Tulip breaking virus | TBV |
| Turnip mosaic virus (6 strains tested) | TuMV |
| Watermelon mosaic virus | WMV-II |
| Zucchini yellow mosaic virus | ZYMV |

We claim:

1. A continuous hybridoma cell line capable of secreting monoclonal antibodies specifically reactive with an epitope found on at least 26 distinct potyvirus types of the potyvirus group and insignificantly reactive with other plant viruses, said epitope specifically bound by the monoclonal antibody produced by cell line ATCC HB 9452.

2. The hybridoma of claim 1, wherein said hybridoma is ATCC HB 9452 and its isotype switch variants.

3. A monoclonal antibody specifically reactive with an epitope found on at least 26 distinct potyvirus types of the potyvirus group and insignificantly reactive with other plant viruses, said epitope specifically bound by the monoclonal antibody produced by cell line ATCC HB 9452.

4. The monoclonal antibody, according to claim 3, wherein said monoclonal antibody is produced by cell line ATCC HB 9452.

5. A method of detecting a potyvirus which comprises contacting a source suspected of containing a potyvirus, or a potyvirus antigen, with a diagnostically effective amount of a monoclonal antibody, or specific binding fragment thereof, wherein said monoclonal antibody is specifically reactive with an epitope found on at least 26 distinct potyvirus types of the potyvirus group and is insignificantly reactive with other plant viruses, and detecting said antibody bound to said epitope, wherein said epitope is specifically bound by the monoclonal antibody produced by cell line ATCC HB 9452.

6. The method of claim 5, wherein said antibody is produced by cell line ATCC HB 9452.

7. The method of claim 5, wherein said monoclonal antibody is detectably labled.

8. The method of claim 7, wherein said detectable label is selected from the group consisting of a radioisotope, a fluorescent compound, a colloidal metal, a chemiluminescent compound, a bioluminescent compound and an enzyme.

* * * * *

UNITED STATES PATENT AND TRADEMARK OFFICE
CERTIFICATE OF CORRECTION

PATENT NO. : 5,043,263
DATED : August 27, 1991
INVENTOR(S) : John Hammond, et al It is certified that error appears in the above-identified patent and that said Letters Patent is hereby corrected as shown below:

Title page, item [76], reverse the order of the inventors to read as follows:

Raymond L. Jordan, Jr., 8715 Clemente Ct., Jessup, Md. 20794

John Hammond, 9217 Twin Hill La., Laurel, Md. 20708

Signed and Sealed this

Twentieth Day of April, 1993

Attest:

MICHAEL K. KIRK

*Attesting Officer*    Acting Commissioner of Patents and Trademarks